(12) United States Patent
Iida et al.

(10) Patent No.: US 6,204,002 B1
(45) Date of Patent: Mar. 20, 2001

(54) GANGLIOSIDES HAVING FLUORESCENT-TAGGED CERAMIDE MOIETIES

(75) Inventors: Takao Iida; Yutaka Ohira, both of Tsukuba (JP)

(73) Assignee: Daikin Industries, Ltd. (JP)

( * ) Notice: Subject to any disclaimer, the term of this patent is extended or adjusted under 35 U.S.C. 154(b) by 0 days.

(21) Appl. No.: 09/091,780

(22) PCT Filed: Oct. 22, 1997

(86) PCT No.: PCT/JP97/03810

§ 371 Date: Dec. 23, 1998

§ 102(e) Date: Dec. 23, 1998

(87) PCT Pub. No.: WO98/17674

PCT Pub. Date: Apr. 30, 1998

(30) Foreign Application Priority Data

Oct. 22, 1996 (JP) .................................................. 8-279725

(51) Int. Cl.$^7$ ..................... G01N 33/533; G01N 33/556; C07H 15/00

(52) U.S. Cl. .................. 435/7.25; 435/7.92; 435/975; 436/546; 436/800; 436/811; 436/818; 536/17.2; 536/17.9

(58) Field of Search ................... 436/546, 811, 436/800; 435/7.25, 7.92, 975; 536/17.2, 17.9

(56) References Cited

U.S. PATENT DOCUMENTS

| | | | |
|---|---|---|---|
| 4,784,811 | * 11/1988 | Hirschfeld | 264/1.4 |
| 5,375,606 | * 12/1994 | Slezak et al. | 128/691 |
| 5,550,025 | * 8/1996 | Walker | 435/6 |
| 5,573,909 | 11/1996 | Singer et al. | 435/6 |
| 5,583,208 | 12/1996 | Iida et al. | 536/17.9 |
| 5,667,764 | * 9/1997 | Kopia et al. | 424/1.45 |
| 5,773,596 | 6/1998 | Iida et al. | 536/18.6 |

FOREIGN PATENT DOCUMENTS

| 07309888 | * 11/1995 | (JP) . |
|---|---|---|
| WO95/32211 | 11/1995 | (WO) . |

OTHER PUBLICATIONS

"Synthesis of a Ganglioside GM$_3$ Position Isomer, N–Acetylneuraminosyl–α–(2→6)–lactosyl–β(1→1)–ceramide", Hasegawa et al, *Biosci. Biotech. Biochem.*, 56(3), pp. 535–536, 1992.

"The Use of a Phospholipid Analogue of Diphenyl–1,3,5–Hexatriene to Study Melittin–Induced Fusion of Small, Unilamellar Phospholipid Vesicles", Morgan et al, *Biochimica et Biophysica Acta*, 692, pp. 196–201, 1982.

*Tosakenkyunosaisentan*, pp. 129–148 (1996) and partial English translation relating to p. 141, lines 7–3 from the bottom.

"Diphenylhexatrienylpropanoylhydrazyl stachyose: a new oligosaccharide derivative of diphenylhexatriene. Synthesis and fluorescence properties in artificial membranes", Ivessa et al, *Chem. Phys. Lipids*, vol. 49, No. 3, pp. 185–95, (1988).

"Interaction of influenza virus with gangliosides and liposomes containing gangliosides", Slepushkin et al, *Eur. J. Biochem.*, vol. 173, No. 3, pp. 599–605, (1988).

* cited by examiner

Primary Examiner—Mary E. Ceperley
(74) Attorney, Agent, or Firm—Larson & Taylor, PLC

(57) ABSTRACT

The invention provides a compound represented by the following formula (I)

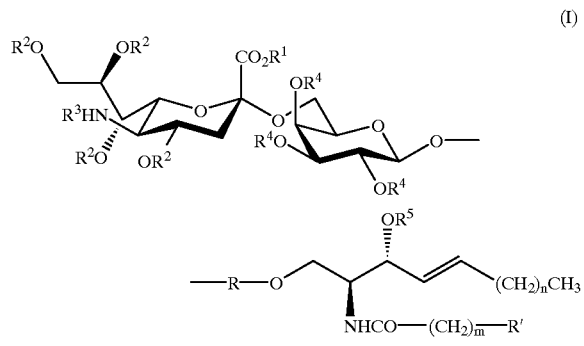

wherein m is an integer of 2–15; n is an integer of 0–12; R represents a sugar chain or a derivative thereof; R' represents a general formula (II)

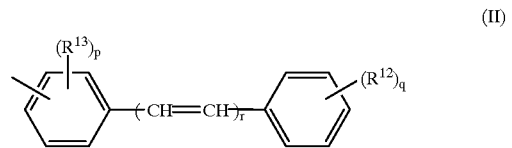

(wherein p is an integer of 0–4, q is an integer of 0–5; r is an integer of 2–5; $R^{12}$ and $R^{13}$ are the same or different and each represents a hydrogen atom, a lower alkyl group, an aliphatic acyl group, a nitro group or a nitrile group), $R^1$ represents a hydrogen atom or a protective group of carboxylic acid, $R^2$, $R^4$ and $R^5$ are the same or different and each represents a hydrogen atom, an aliphatic or aromatic acyl group; $R^3$ represents an acetyl group, a glycolyl group or a trifluoroacetyl group; useful as reagent for detecting influenza virus A.

6 Claims, 1 Drawing Sheet

GANGLIOSIDES HAVING FLUORESCENT-TAGGED CERAMIDE MOIETIES

FIELD OF THE INVENTION

The invention relates to gangliosides whose ceramide moieties are labeled with fluorescence and synthetic intermediates thereof, and an reagent and kit for detecting an influenza viruses.

BACKGROUND ART

Glycolipids from mammalian cells belong to sphingo-glycolipides comprising a lipid portion, so-called ceramide, composed of sphingosine to which long chain fatty acid is bound by an amide bond, a variety of oligosaccharide chains and a sialic acid. Ganglioside is a general term of sphingo-glycolipides comprising a sialic acid. Recent research has proved that, in general, a sialyl sugar chain of ganglioside, most parts of which are located on the surface of animal cells, is oriented outward from the cell surface so as to play an important role in basic vital phenomenons such as cell discrimination, acceptance and response of information, receptor functions to hormones, viruses, bacteria, cytotoxins and so on, intercellular recognition, and also, differentiation, growth, canceration and immunity of cells.

Within the sugar chains, it is found that hemagglutinin, which comprises virus membrane of influenza virus A, is very effectively bound to a ganglioside comprising a five-sugar chain containing a sialyl($\alpha$2-6)galactose sugar chain (see, Japanese Unexamined Patent Publication No. H6-247995).

It is considered that novel means may be provided in the field of research on influenza virus by synthesizing fluorescent derivatives having a hemagglutinin binding activity similar to said ganglioside and resistance to sialidase on the surface of membrane of influenza virus.

It is found that influenza viruses bind to a sialic acid-containing sugar chain which is included in glycolipids and glycoproteins. Influenza viruses are classified in A-, B- and C-types. Viruses A and B are bound to an N-acetylneuraminic acid- or N-glycolylneuraminic acid-containing sugar chain, and virus C is bound to a 9-O-acetylsialic acid-containing sugar chain, by intervention of hemagglutinin therebetween. In particular, influenza virus A is potently infectious so that a clinical importance of this type of discrimination is widely recognized.

Radioisotope methods, which are used for probe of a phenomenon that bacteria, bacteria-generating toxins and viruses are bound to glycolipids, have problems of (1) health care of researchers, (2) necessity of special facilities or systems, (3) necessity of a person in charge of treatment radioisotope, (4) waste disposal and (5) long half-life of radioisotope. In addition, increase of radioactivity is limited, since a higher specific activity of radioactive probe promotes autoclasis of probe. It is said that improvement of detection limit is difficult based on the principle. In recent years, development of techniques on radiationless isotope have been given importance to so that the fluorescent method is regarded as effective.

Production of fluorescence-labeled glycolipid containing a sialyl sugar chain will be useful, since the sugar chain may be used as a reagent for detection, identification and diagnosis of influenza virus A which is infectious. Specifically, it is considered that novel means may be provided in the field of research of interaction between viruses and cells by synthesizing derivatives into which fluorochrome is introduced at a site of lipid portion which is not related to binding of glycolipid to a receptor, and derivatives which retain a native binding activity of influenza virus A to hemagglutinin, which makes it possible to detect and identify viruses as receptor, and to trace its behavior visually.

From the viewpoint, the inventors have already synthesized GM3 which has fluorescein at a ceramide moiety (see, Japanese Unexamined Patent Publication No. H7-309888). However, it was revealed by examination of fluorescence of the obtained compounds that virus-bound GM3 fluorescein had very weak fluorescence in hydrophobic conditions (conditions to determine fluorescence using a densitometer with the adhesion of GM3 to a microplate), which was insufficient to detect influenza virus.

Furthermore, hemaggultinin of influenza virus tends to recognize a sialyl($\alpha$2-6)galactose bond rather than a sialyl ($\alpha$2-3)galactose bond of GM3 (TOSAKENKYU NO SAISENTAN (FUKUDA Minoru Ed.; YOSUISYA), page 141, 1996).

As shown above, it is necessary to inspect a variety of derivatives having a binding activity to sialyl($\alpha$2-6) galactose and fluorochrome which does not depend on detection environment.

It is an object of the invention to provide ganglioside derivatives (I) and (V), which have a binding activity to hemagglutinin on the surface of membrane of influenza virus A and fluorochrome to maintain fluorescent properties in hydrophobic conditions, and synthetic intermediates thereof.

Furthermore, it is another object of the invention to provide a reagent to detect influenza viruses using the derivatives.

DISCLOSURE OF THE INVENTION

Figure 1:
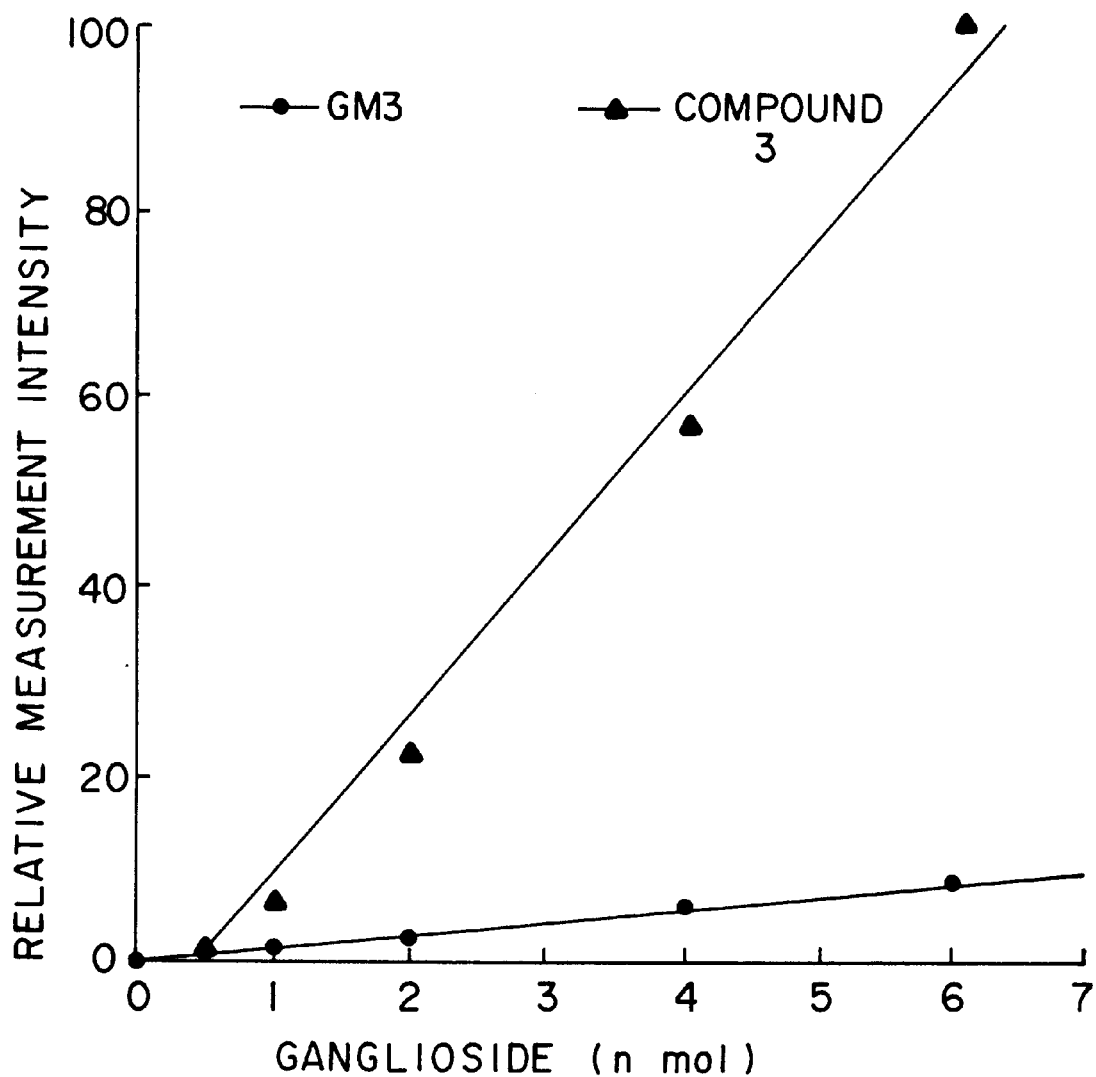
FIG. 1 shows results of determination of binding activities of the compound 3 (▲) of the invention and GM3 (sialyl ($\alpha$2-3)lactosylceramide;●) to influenza virus A/Aichi/2/68 (H3N2).

A method for labeling and modifying a fatty acid residue which constitutes an amide bond of ceramide moiety is used, since a stable bonding under deprotection conditions is necessary to obtain compounds (I) and (V). It is necessary that the number of atoms between an amide bond of ceramide and a fluorochrome is 2–20 (comprising carbon, oxygen, nitrogen, sulfur, phophorus etc., preferably 2–10). A variety types of the fluorochrome may be used.

The inventors conducted research on ganglioside derivatives having a binding activity to influenza virus A and fluorescent properties which are not decreased during operation for simple detection and diagnosis and found that derivatives into which fatty acids with hydrophobic diphenylhexatriene fluorochrome in place of fatty acid of ceramide are introduced sufficiently bind to influenza virus, in particular, influenza virus A and whose fluorescence properties are not changed in dry conditions. The invention has been accomplished based on the findings.

Thus, the invention relates to the following gangliosides and synthetic intermediates thereof, and a reagent and kit for detecting influenza viruses using the gangliosides.

1. A compound represented by the following formula (I)

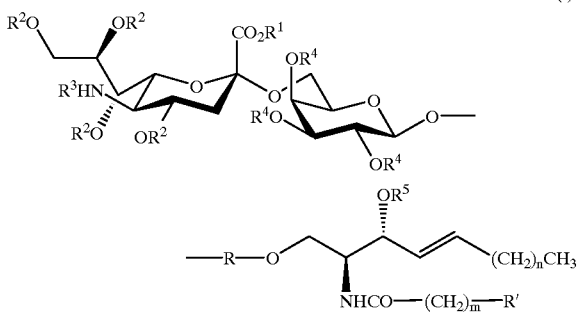

(I)

wherein m is an integer of 2–15; n is an integer of 0–12; R represents a sugar chain or a derivative thereof; R' represents a general formula (II)

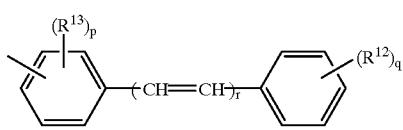

(II)

(wherein p is an integer of 0–4, q is an integer of 0–5; r is an integer of 2–5; $R^{12}$ and $R^{13}$ are the same or different and each represents a hydrogen atom, a lower alkyl group, an aliphatic acyl group, a nitro group or a nitrile group), $R^1$ represents a hydrogen atom or a protective group of carboxylic acid, $R^2$, $R^4$ and $R^5$ are the same or different and each represents a hydrogen atom, an aliphatic or aromatic acyl group; $R^3$ represents an acetyl group, a glycolyl group or a trifluoroacetyl group.

2. The compound according to item 1 wherein O—R— is any one of sugar chain or a derivative thereof selected from the group consisting of 4-O-β-D-glucopyranosyl;
3-O-β-D-glucopyranosyl;
4-O-2-acetamido-2-deoxy-β-D-glucopyranosyl;
3-O-2-acetamido-2-deoxy-β-D-glucopyranosyl;
4-O-(2-acetamido-2-deoxy-β-D-glucopyranosyl)-(1→3)-O-(β-D-galactopyranosyl)-(1→4)-O-β-D-glucopyranosyl;
4-O-(2-acetamido-2-deoxy-β-D-glucopyranosyl)-(1→4)-O-(β-D-galactopyranosyl)-(1→3)-O-β-D-glucopyranosyl;
4-O-(2-acetamido-2-deoxy-β-D-glucopyranosyl)-(1→3)-O-(β-D-galactopyranosyl)-(1→3)-O-β-D-glucopyranosyl;
4-O-(2-acetamido-2-deoxy-β-D-glucopyranosyl)-(1→4)-O-(β-D-galactopyranosyl)-(1→4)-O-β-D-glucopyranosyl;
3-O-(2-acetamido-2-deoxy-β-D-glucopyranosyl)-(1→3)-O-(β-D-galactopyranosyl)-(1→4)-O-β-D-glucopyranosyl;
3-O-(2-acetamido-2-deoxy-β-D-glucopyranosyl)-(1→4)-O-(β-D-galactopyranosyl)-(1→3)-O-β-D-glucopyranosyl;
3-O-(2-acetamido-2-deoxy-β-D-glucopyranosyl)-(1→3)-O-(β-D-galactopyranosyl)-(1→3)-O-β-D-glucopyranosyl; and
3-O-(2-acetamido-2-deoxy-β-D-glucopyranosyl)-(1→4)-O-(β-D-galactopyranosyl)-(1→4)-O-β-D-glucopyranosyl 3. A sialyl(α2-6)lactosylceramide according to item 1 represented by the following formula (V):

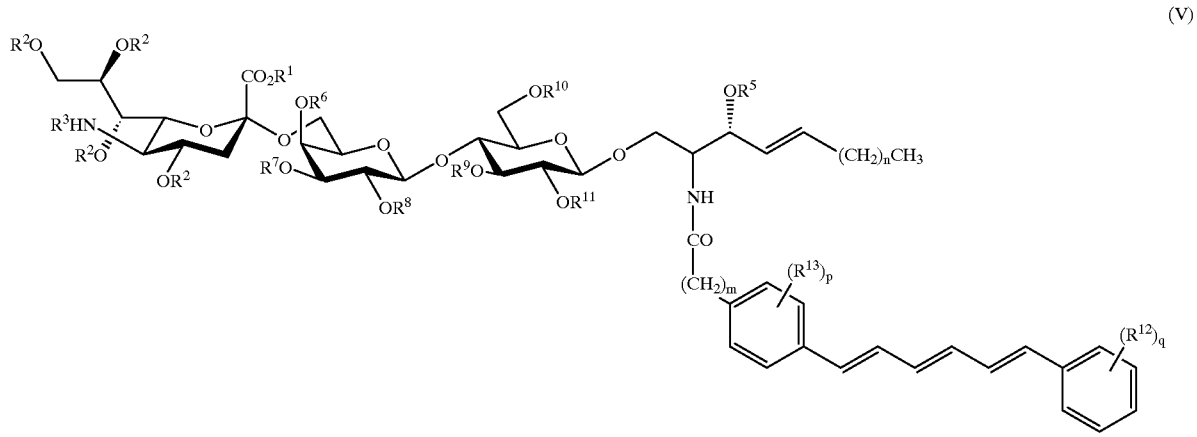

(V)

wherein m is an integer of 2–15; n is an integer of 0–12; p is an integer of 0–4; q is an integer of 0–5; $R^1$ represents a hydrogen atom or a protective group of carboxylic acid; $R^2$ and $R^5$–$R^{11}$ are the same or different and each represents a hydrogen atom, aliphatic or aromatic acyl group or a hydroxyl protective group; $R^{12}$ and $R^{13}$ are the same or different and each represents a hydrogen atom, a lower alkyl group, a aliphatic acyl group, a nitro group or a nitrile group. $R^3$ represents an acetyl group, a glycolyl group or a trifluoroacetyl group.

4. Use of the compound according to any one of items 1–3 to detect an influenza virus.
5. A reagent for detecting an influenza virus comprising the compound according to any one of items 1–3.
6. A kit for detecting an influenza virus comprising the compound according to any one of items 1–3 as a reagent for detecting the influenza virus.
7. The kit for detecting an influenza virus according to item 6 which further comprises a PBS buffer, a microplate, an erythrocyte, an anti-influenza antibody and a peroxidase-labeled protein A.

The compound of the invention is useful as a reagent for detecting an influenza virus, in particular, useful for detecting influenza virus A.

Examples of lower alkyl group represented by $R^{12}$ and $R^{13}$ are methyl, ethyl, n-propyl, isopropyl, n-butyl, isobutyl, sec-butyl, tert-butyl and like alkyl group having 1–4 carbon atoms.

Examples of aliphatic acyl group represented by $R^2$ and $R^4$–$R^{13}$ are formyl, acetyl, propionyl, butylyl, iosobutylyl, valeryl, isovaleryl, pivaloyl and like aliphatic acyl group having 2–5 carbon atoms, preferably an acetyl group.

Examples of protective group of carboxylic acid represented by $R^1$ are methyl, ethyl, n-propyl, isopropyl, n-butyl, isobutyl, sec-butyl, tert-butyl and like lower alkyl group, an optionally substituted phenyl group and an optionally substituted benzyl group.

Examples of aromatic acyl group represented by $R^2$ and $R^4$–$R^{11}$ are benzoyl groups which may have 1–3 substituents such as a lower alkyl group having 1–4 carbon atoms, a methoxy group, an ethoxy group, a hydroxyl group, a methylenedioxy group, an amino group, mono-$C_1$–$C_4$ lower alkyl- or di-($C_1$–$C_4$ lower alkyl)-amino group, a nitro group, a nitrile group, a chlorine atom, a bromine atom and a fluorine atom.

Examples of the sugar chain represented by O—R— are:

4-O-β-D-glucopyranosyl;
3-O-β-D-glucopyranosyl;
4-O-2-acetamido-2-deoxy-β-D-glucopyranosyl;
3-O-2-acetamido-2-deoxy-β-D-glucopyranosyl;
4-O-(2-acetamido-2-deoxy-β-D-glucopyranosyl)-(1→3)-O-(β-D-galactopyranosyl)-(1→4)-O-β-D-glucopyranosyl;
4-O-(2-acetamido-2-deoxy-β-D-glucopyranosyl)-(1→4)-O-(β-D-galactopyranosyl)-(1→3)-O-β-D-glucopyranosyl;
4-O-(2-acetamido-2-deoxy-β-D-glucopyranosyl)-(1→3)0-(β-D-galactopyranosyl)-(1→3)-O-β-D-glucopyranosyl;
4-O-(2-acetamido-2-deoxy-β-D-glucopyranosyl)-(1→4)-O-(β-D-galactopyranosyl)-(1→4)-O-β-D-glucopyranosyl;
3-O-(2-acetamido-2-deoxy-β-D-glucopyranosyl)-(1→3)-O-(β-D-galactopyranosyl)-(1→4)-O-β-D-glucopyranosyl;
3-O-(2-acetamido-2-deoxy-β-D-glucopyranosyl)-(1→4)-O-(β-D-galactopyranosyl)-(1→3)-O-β-D-glucopyranosyl;
3-O-(2-acetamido-2-deoxy-β-D-glucopyranosyl)-(1→3)-O-(β-D-galactopyranosyl)-(1→3)-O-β-D-glucopyranosyl; and
3-O-(2-acetamido-2-deoxy-β-D-glucopyranosyl)-(1→4)-O-(β-D-galactopyranosyl)-(1→4)-O-β-D-glucopyranosyl;

Preferable sugar chains are

4-O-β-D-glucopyranosyl;
3-O-β-D-glucopyranosyl;
4-O-2-acetamido-2-deoxy-β-D-glucopyranosyl;
3-O-2-acetamido-2-deoxy-β-D-glucopyranosyl; and
3-O-(2-acetamido-2-deoxy-β-D-glucopyranosyl)-(1→3)-O-(β-D-galactopyranosyl)-(1→4)-O-β-D-glucopyranosyl;

Said sugar chain derivatives relating to O—R— are compounds, at least one hydrogen atom of hydroxyl group of sugar chain of which is substituted by a aliphatic acyl group or an aromatic acyl group as defined above, preferably by an acetyl group or a benzoyl group.

With respect to the compound of formula (I) of the invention, $R^1$ is preferably a hydrogen atom, a methyl group, an ethyl group, a tert-butyl group or a benzyl group.

$R^{12}$ and $R^{13}$ are preferably an hydrogen atom, a methyl group or an acetyl group.

$R^2$, $R^4$ and $R^6$–$R^{11}$ are preferably a hydrogen atom or an acetyl group, more preferably a hydrogen atom.

$R^3$ is preferably an acetyl group or a glycolyl group, more preferably an acetyl group.

$R^5$ is preferably a hydrogen atom or a benzoyl group. p is an integer of 0–4, preferably 0 or 1, more preferably 0.

q is an integer of 0–5, preferably 0 or 1, more preferably 0.

r is an integer of 2–5, preferably 3.

The compound of the invention having r number of double bonds in R' group includs a number of stereoisomers, since each of double bonds may be either trans or cis. Preferable compounds are compounds in which all double bonds are trans-type.

According to the invention, particularly preferable compound (compound 3) is shown below.

Compound 3

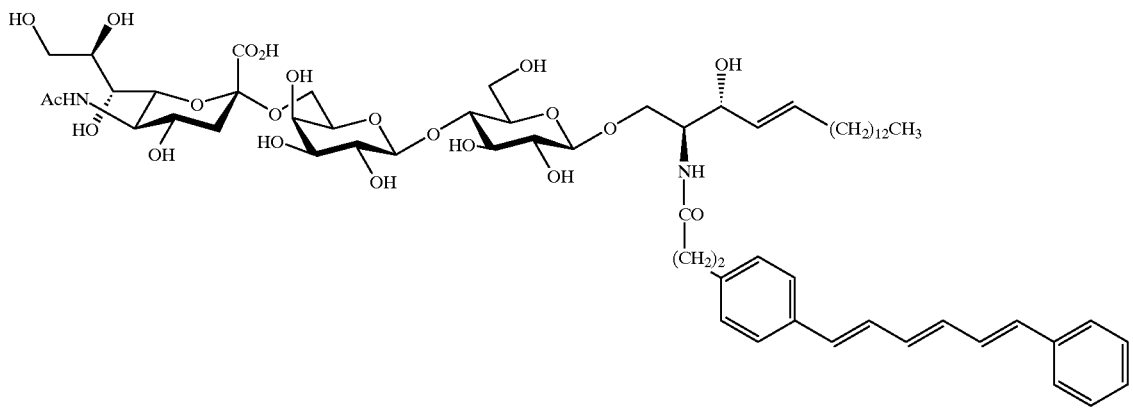

Each compound of the invention represented by formulae (I) and (V) may be produced according to <Reaction formula 1> and <Reaction formula 2> below.

(Step B)
The compound of formula (V) may be obtained by reacting the compound of formula (III) and the compound of Reaction formula 1

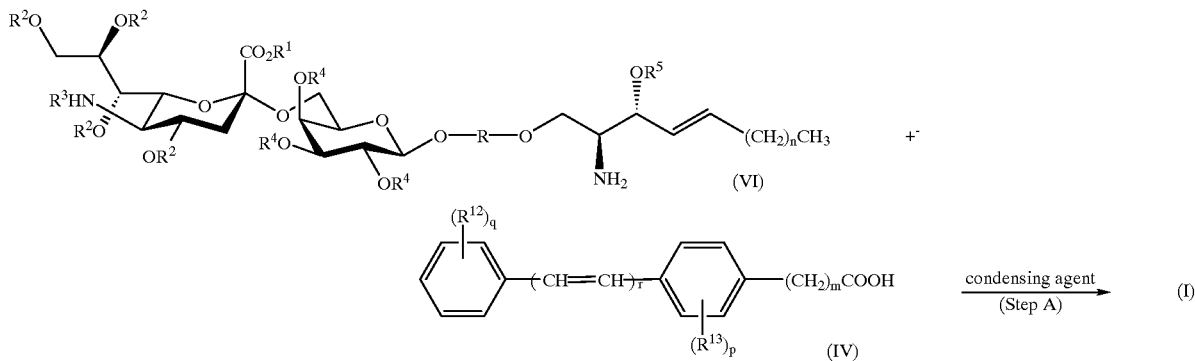

wherein n, m, p, q, r, R, $R^1$–$R^5$, $R^{12}$ and $R^{13}$ are defined above.

formula (IV) in a solvent in the presence of a condensing agent, followed by optionally deprotecting the resulting Reaction formula 2

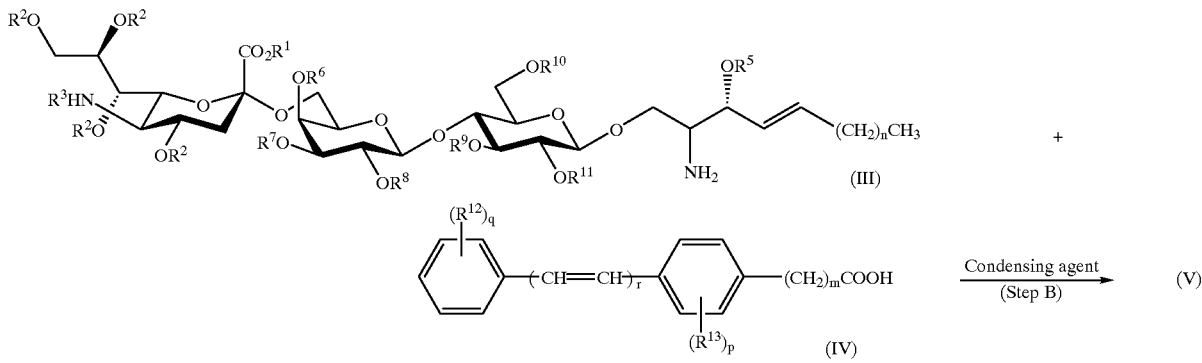

wherein n, m, p, q, $R^1$–$R^3$ and $R^5$–$R^{13}$ are as defined above.
(Step A)
The compound of formula (I) may be obtained by reacting a compound of formula (VI) and a compound of formula (IV) in a solvent in the presence of a condensing agent, followed by optionally deprotecting the resulting compound. The solvent includes DMF, ethyl acetate, chloroform, dichloromethane, THF and formamide. The comdensing agent includes DCC, water soluble carbodiimide (WSC) and carbonyldiimidazole. In carrying out the invention, the molar amount of the compound of formula (IV) is about 1–1.1 times, and the molar amount of the condensing agent is about 1–1.1 times as much as the molar amount of the compound of formula (VI) in a solvent. The reaction temperature is from room temperature to around boiling point of solvent, and the reaction time is about 1–24 hours. The conditions are favorable to the progress of the reaction. When deprotection (ester hydrolysis) of hydroxyl group such as acetyl group is conducted, the reaction may be carried out by using 1 equivalent to excessive amount of alkali (sodium methoxide, sodium ethoxyde, NaH, etc. in alcohols, and sodium hydroxide, potassium hydroxide, etc. in aqueous solution ) in a solvent such as methanol, ethanol and like alcohols, and water.

compound. The compound of formula (V) may be obtained in the same manner as said <reaction formula 1> with respect to condensing agent, solvent, reaction time, reaction temperature and proportion of used reagents except that the compound of formula (III) is used in place of the compound of formula (VI).

Said compounds of formulae (III) and (VI) are known, and may be prepared according to the disclosures of Japanese Unexamined Patent Publication No. H7-309888 and Japanese Unexamined Patent Publication No. H6-247995.

The compound of formula (IV) may be obtained according to <reaction formula 3> based on the disclosure of Biochimica et Biophysica Acta, 692, 196–201 (1982).

Reaction formula 3

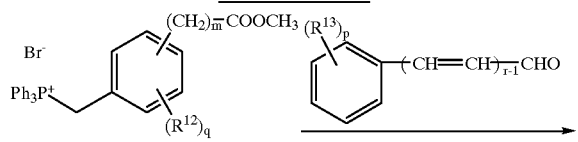

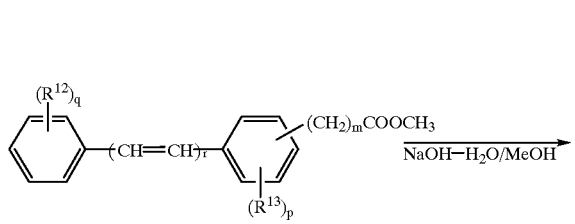
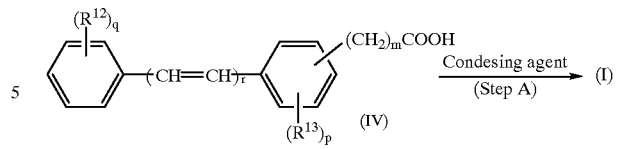
wherein m, p, q, r, $R^{12}$ and $R^{13}$ are as defined above. For reference, a synthetic route of compound 3 described in the examples are shown in <reaction formula 4>
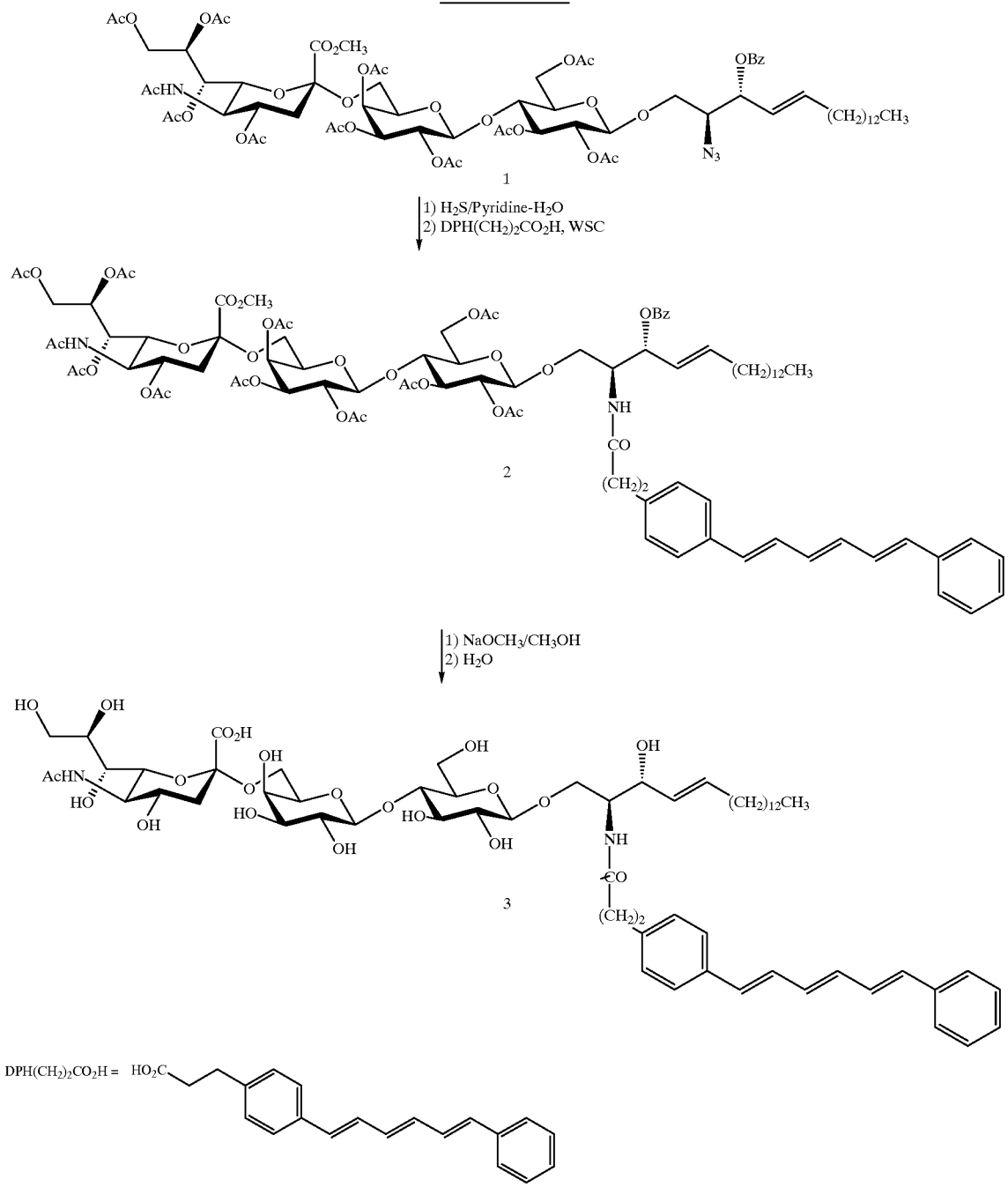

wherein "Ac" is an acetyl group and "Bz" is a benzoyl group.

Compound 1 is described in Hasegawa et al., Biosci. Biotech. Biochem., 56, 535–536 (1992). Synthesis of 3-(p-(6-phenyl)1,3,5-hexatrienyl)phenylpropionic acid may be conducted according to Biochimica et Biophysica Acta, 692, 196–201 (1982).

The compound of the invention provides means to simply detect and identify influenza viruses A and B whose virus membranes have hemagglutinin in a sample infected by the viruses. It is found that the compound is particularly useful as a reagent and kit for detection and diagnosis of potently infectious influenza virus A. In addition, the compound may be used as a reagent and kit for tracing dynamic behavior of sugar chain receptor of the viruses.

The kit of the invention comprises the compound of formula (I), a PBS buffer, a microplate, an erythrocyte, an anti-influenza antibody, a peroxidase-labeled protein A, etc. The agents except for the compound of formula (I) may be commercially available. The amount of each ingredient may be easily determined by those skilled in the art by referring to the following example 3.

The invention will be described below in greater detail using examples, but the invention is in no way limited to the examples.

BEST MODE FOR CARRYING OUT THE INVENTION

EXAMPLE 1

Synthesis of O-(methyl 5-acetamide-4,7,8,9-tetra-O-acetyl-3,5-dideoxy-D-glycero-β-D-galacto-2-nonuropyranosylonate)-(2-6)-O-(2,3,4-tri-O-acetyl-β-D-gal actopyranosyl)-(1→4)-O-(2,3,6-tri-O-acetyl-β-D-glucopyran osyl)-(1→1)-(2S, 3R, 4E)-3-O-benzoyl-2-(3-(p-(6-phenyl)1, 3,5-hexatrienyl) phenylpropionamide)-4-octadecene-1,3-diol (compound 2)

O-(methyl 5-acetamido-4,7,8,9-tetra-O-acetyl-3,5-dideoxy-D-glycero-α-D-galacto-2-nonuropyranosylonate)-(2→6)-O-(2,3,4-tri-O-acetyl-β-D-gal actopyranosyl)-(1→4)-O-(2,3,6-tri-O-acetyl-β-D-glucopyran osyl)-(1→1)-(2S, 3R, 4E)-2-azide-3-O-benzoyl-4-octadecene-1,3-diol (compound 1) (130 mg, 0.088 mmol) was dissolved in 14.4 ml of 83% aqueous pyridine solution through which hydrogen sulfide gas was bubbled at room temperature for 29 hours. After ascertainment of disapperance of starting material, hydrogen sulfide was first removed from the reaction mixture, and then pyridine and water were evaporated in vacuo. The residue was dissolved in 7 ml of dry dichloromethane. Under argon atmosphere, 40 mg (0.17 mmol) of 3-(p-(6-phenyl)1,3,5-hexa trienyl)phenylpropionic acid and 1-ethyl-3-(3-dimethylaminopropyl)carbodiimide hydrochloride (50 mg, 0.26 mmol) were added to the solution, and the mixture was stirred at room temperature for 18 hours. The reaction mixture was diluted with 70 ml of dichloromethane, washed with water, dried over dry sodium sulfate and concentrated under reduced pressure. The residue thus obtained was subjected to a silica gel column chromatography (packing: silica gel 60(7734), eluent: ethyl acetate/hexane=3/1) to give 98 mg of compound 2. Yield 64%.

$[\alpha]_D^{25}$ −9.3 (c 2.4, CHCl$_3$)

IR$^{KBR}_{max}$cm$^{-1}$: 3400(NH), 1750, 1220(ester), 1670, 1540 (amide), 720(Ph)

NMR(CDCl$_3$), TMS): $_\delta$0.88(t, 3H, J=6.2 Hz, CH$_3$ CH$_2$), 1.25(s, 22H, 11CH$_2$), 1.89(s, 3H, AcN), 2.55(dd, 1H, J$_{3a,3e}$=12.8 Hz, J$_{3e,4}$=4.4 Hz, H-3e(sial)), 3.75(s, 3H, MeO), 4.45(d, 1H, J$_{1,2}$=7.7 Hz, H-1(Glc)), 4.53(d, 1H, J$_{1,2}$=7.3 Hz, H-1(Gal)), 4.97(dd, 1H, J$_{2,3}$=10.5 Hz, J$_{3,4}$=3.3 Hz, H-3 (Gal)), 5.06(dd, 1H, J$_{2,3}$=10.5 Hz, J$_{1,2}$=7.3 Hz, H-2(Gal)), 5.21(dd, 1H, J$_{6,7}$=2.9 Hz, J$_{7,8}$=9.5 Hz, H-7(sial)), 5.78(d, 1H, NH), 5.85(dt, 1H, J$_{4,5}$=14.1 Hz, J$_{5,6}$=7.1 Hz, H-5 (sphingosine)), and 6.45–8.05(m, 20H, Ph and trans-CH=CH).

EXAMPLE 2

Synthesis of O-(5-acetamide-3,5-dideoxy-D-glycero-α-D-galacto-2-nonuropyranosylonate)-(2→6)-O-(β-D-galactopyran osyl)-(1→4)-O-(β-D-glucopyranosyl)-(1→1)-(2S, 3R,4E)-2-(3-(p-(6-phenyl)1,3,5-hexatrienyl)phenylpropionamide)-4-octadecene-1,3-diol(compound 3)

Compound 2 (88 mg, 0.051 mmol) was dissolved in 5 ml of dry methanol. Under argon atmosphere, 20 mg of sodium methoxide was added to the solution, and the mixture was stirred at room temperature for 5.5 hours. After cooling to 0° C., 0.5 ml of water was added to the solution and then stirred at room temperature for 12 hours. The mixture was subjected to Amberlite IR120(H$^+$) column chromatography (eluent: methanol). The eluate was concentrated under reduced pressure. The residue was subjected to a column chromatography (packing: Sephadex LH-20, eluent: methanol-water=1:1) to obtain 28 mg of compound 3. Yield 43%.

$[\alpha]_D^{25}$+8.5 (c 0.18, 1:1 methanol-water)

IR$^{KBr}_{max}$cm$^{-1}$: 3700-3200(OH, NH), 2920, 2850(Me, methylene), 1730(carbonyl), 1640, 1560(amide), 1070 (ether), 750(Ph)

NMR(1:1 CD$_3$OD-CDCl$_3$): δ0.89(t, 3H, J=6.2 Hz, CH$_3$ CH$_2$), 1.28(s, 22H, 11CH$_2$), 1.99(s, 3H, AcN), 2.16(dd, 1H, J$_{3a,3e}$=J$_{3e,4}$=11.7 Hz,H-3e(sial)), 2.79(dd, 1H, J$_{3a,3e}$11.7 Hz, J$_{3e,4}$=4.4 Hz, H-3e(sial)), 5.43(dd, 1H, J$_{3,4}$=7.2 Hz, J$_{4,5}$=15.5 Hz, H-4(sphingosine)), 5.68(dt, 1H, J$_{4,5}$==15.45 Hz, J$_{5,6}$= 7.0 Hz, H-5(sphingosine)) and 6.5–8.1(m, 15H, Ph and trans-CH=CH).

EXAMPLE 3

Determination of binding activity of sialyl(α2-6) lactose derivative(compound 3) to influenza virus The binding activity of sialyl(α2-6)lactose derivative (compound 3) to influenza virus was determined (TLC/virus binding assay) to find usufulness thereof as a reagent for detecting influenza virus.
Material of Experiment
Influenza virus used: A/Aichi/2/68(H3N2)

Comparative compound of binding activity: sialyl (α2-3)lactosylceramide (GM3)

Each ganglioside, compound 3 and GM3 (0.5, 1, 4, 6 nmol) were spotted on silica gel thin layer plate (5×5 cm; Polygram SIL G, Marchery, Nsgel), which was developed with chloroform/methanol/12 mM aqueous magnesium chloride solution (5:4:1) (V/V). After air-drying, blocking of the plate was conducted by gradually dipping the plate into a PBS(phosphate buffer containing 0.9% sodium chloride) solution containing 1% ovalbumin and 1% poly (vinylpyrrolidone) (PVP) (Solution A) at 37° C. for 3 hours. After washing the plate for 5 times with PBS, influenza viruses were diluted by sequential two-fold dilution with 0.01% gelatin-PBS solution on HAU (Hemagglutinin unit)

(erythrocyte aggregation activity) microplate (96U-bottom wells, product of Falcon). 0.5% (V/V) chicken erythrocyte-PBS floating solution was added thereto, and the mixture was reacted at 4° C. for 1 hour. HAU was represented by the maximum dilution factor of viruses which was necessary for aggregation of chicken erythrocyte. 3 ml of $2^8$ influenza viruses (A/Aichi/2/68 (H3N2)-PBS suspension was added thereto, and the mixture was reacted with shake at 4° C. overnight. After washing the plate for 5 times with PBS, 3 ml of rabbit anti-influenza virus antibody diluted 1,000-fold with 3% PVP/PBS (Solution B) was added thereto, and the mixture was shaken at 4° C. for 2 hours. After washing the plate for 5 times with PBS, the plate was blocked with Solution A at 4° C. for 30 minutes. After further washing the plate for 5 times with PBS, 3 ml of horseradish peroxidase-labeled protein A (product of Oganon Teknika Corp.) diluted 1,000-fold with solution B was added thereto, and the plate was shaken at 4° C. for 2 hours. After washing the plate for 5 times with PBS, a color producing solution prepared by mixing 110 mM of 4-chloro-1-naphtol in acetnitrile solution (200 µl) and 31% aqueous hydrogen peroxide solution (1 µl) in 10 ml of 0.1 M acetate buffer (pH 6.0) was added thereto, which was shaken for 5 minutes. The plate was washed with distilled water and air-dried to determine color development with densitometer (product of SHIMAZU, CS-9000) at measurement wavelength of 620 nm and reference wavelength of 430 nm. In FIG. 1, relative measurement intensity at each concentration of ganglioside is indicated as (%) (Response of densitometer at 620 nm)–(response of densitometer at 430 nm) is equal to 100, when compound 3 is 6 nmol.

As shown above, compound 3 detects influenza virus with very high sensitivity.

A/Aichi/2/68 recognizes two bondings, i.e., (α2-3) and (α2-6) whose receptor exists at a ratio of about 1:3. Since compound 3 is 12 times higher than GM3 in detection sensitivity according to FIG. 1, sensitivity of compound 3 is 4 times higher than conventional sialyl (α2-6) lactosylceramide.

It is apparent from said results that the compound of the invention can detect hemagglutinin of influenza A-type virus with high sensitivity.

What is claimed is:

1. A compound represented by the following formula (I)

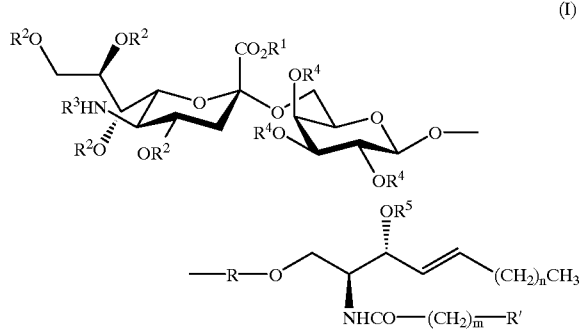

wherein m is an integer of 2–15; n is an integer of 0–12; R represents a sugar chain or a derivative thereof; R' represents a general formula (II)

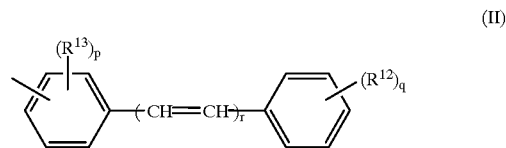

wherein p is an integer of 0–4, q is an integer of 0–5; r is an integer of 2–5; $R^{12}$ and $R^{13}$ are the same or different and each represents a hydrogen atom, a lower alkyl group, an aliphatic acyl group, a nitro group or a nitrile group, $R^1$ represents a hydrogen atom or a protective group of carboxylic acid, $R^2$, $R^4$ and $R^5$ are the same or different and each represents a hydrogen atom, an aliphatic or aromatic acyl group or a hydroxyl protective group; $R^3$ represents an acetyl group, a glycolyl group or a trifluoroacetyl group.

2. The compound according to claim 1 wherein O—R— is selected from the group consisting of 4-O-β-D-glucopyranosyl;

3-O-β-D-glucopyranosyl;

4-O-2-acetamido-2-deoxy-β-D-glucopyranosyl;

3-O-2-acetamido-2-deoxy-β-D-glucopyranosyl;

4-O-(2-acetamido-2-deoxy-β-D-glucopyranosyl)-(1→3)-O-(β-D-galactopyranosyl)-(1→4)-O-β-D-glucopyranosyl;

4-O-(2-acetamido-2-deoxy-β-D-glucopyranosyl)-(1→4)-O-(β-D-galactopyranosyl)-(1→3)-O-β-D-glucopyranosyl;

4-O-(2-acetamido-2-deoxy-β-D-glucopyranosyl)-(1→3)-O-(β-D-galactopyranosyl)-(1→3)-O-β-D-glucopyranosyl;

4-O-(2-acetamido-2-deoxy-β-D-glucopyranosyl)-(1→4)-O-(β-D-galactopyranosyl)-(1→4)-O-β-D-glucopyranosyl;

3-O-(2-acetamido-2-deoxy-β-D-glucopyranosyl)-(1→3)-O-(β-D-galactopyranosyl)-(1→4)-O-β-D-glucopyranosyl;

3-O-(2-acetamido-2-deoxy-β-D-glucopyranosyl)-(1→4)-O-(β-D-galactopyranosyl)-(1→3)-O-β-D-glucopyranosyl;

3-O-(2-acetamido-2-deoxy-β-D-glucopyranosyl)-(1-3)-O-(β-D-galactopyranosyl)-(1→3)-O-β-D-glucopyranosyl; and 3-O-(2-acetamido-2-deoxy-β-D-glucopyranosyl)-(1→4)-O-(β-D-galactopyranosyl)-(1→4)-O-β-D-glucopyranosyl.

3. A sialyl(α2-6)lactosylceramide according to claim 1 represented by the following formula (V):

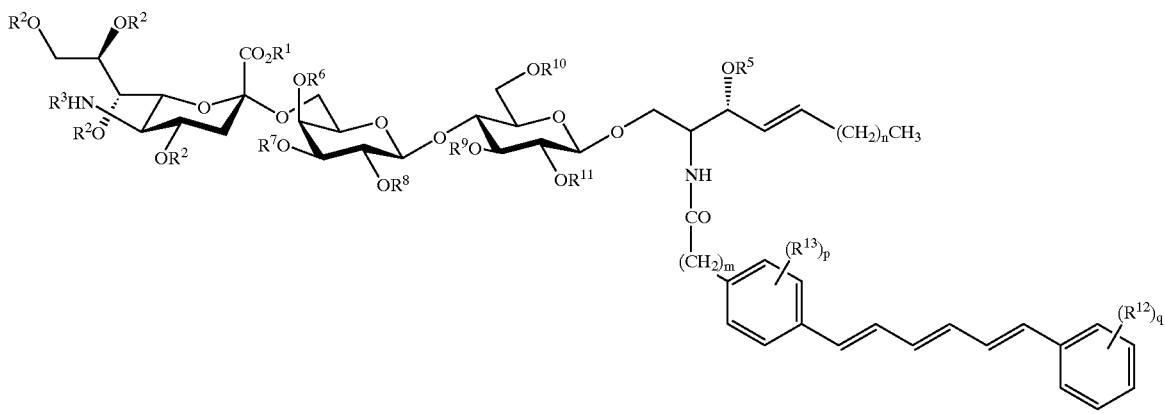

(V)

wherein m is an integer of 2–15; n is an integer of 0–12; p is an integer of 0–4; q is an integer of 0–5; $R^{11}$ are the same or different and each represents a hydrogen atom, aliphatic or aromatic acyl group or a hydroxyl protective group.

4. A reagent for detecting an influenza virus comprising the compound according to claim 1.

5. A kit for detecting an influenza virus comprising the compound according to claim 1 as a reagent for detecting the influenza virus.

6. The kit for detecting an influenza virus according to claim 5 which further comprises a PBS buffer, a microplate, an erythrocyte, an anti-influenza antibody and a peroxidase-labeled protein A.

* * * * *